United States Patent [19]

Bloomfield et al.

[11] Patent Number: 4,488,873
[45] Date of Patent: Dec. 18, 1984

[54] PIEZOELECTRIC POLYMERIC FILM OCCLUSAL FORCE INDICATOR

[75] Inventors: Philip E. Bloomfield, Bala Cynwyd, Pa.; Harry Shpuntoff, Jackson Heights, N.Y.

[73] Assignee: Pennwalt Corporation, Philadelphia, Pa.

[21] Appl. No.: 504,203

[22] Filed: Jun. 14, 1983

[51] Int. Cl.³ .............................................. A61C 9/00
[52] U.S. Cl. ........................................ 433/71; 433/68; 128/777
[58] Field of Search ................... 433/71, 68; 128/642, 128/774, 776, 777, 782

[56] References Cited

U.S. PATENT DOCUMENTS

| | | | |
|---|---|---|---|
| 3,349,489 | 10/1967 | Shackelford | 433/68 |
| 3,604,116 | 9/1971 | Shpuntoff | 433/71 |
| 3,883,954 | 5/1975 | Simmering et al. | 433/68 |
| 3,983,865 | 10/1976 | Shepard | 128/777 |
| 4,334,542 | 6/1982 | Takinishi et al. | 128/777 |
| 4,390,028 | 6/1983 | Okano et al. | 433/71 |

Primary Examiner—John J. Wilson
Attorney, Agent, or Firm—Jordan and Hamburg

[57] ABSTRACT

Dental impression strips prepared from metallized polymer film having piezoelectric properties are coated with a conventional plastically deformable wax impression material to provide the normal visual indication of bite deflection and premature teeth engagement. The metallized polymer film provides means through which force exerted during occlusal analysis may be monitored and recorded. By coating the metallized polymer film with a non-permanently deformable and reusable plastic, the monitoring and recording may readily be demonstrated to the dentist and patient.

13 Claims, 5 Drawing Figures

PIEZOELECTRIC POLYMERIC FILM OCCLUSAL FORCE INDICATOR

STATEMENT OF THE INVENTION

The present invention relates to dental impression devices and more particularly to such a device which includes a transducing piezoelectric polymer film coated with conventional impression wax for providing bite impression data and bite force data.

BACKGROUND AND SUMMARY OF THE INVENTION

Reference is hereby made to U.S. Pat. No. 3,604,116, the subject matter thereof being incorporated herein.

U.S. Pat. No. 3,604,116, issued to H. Shpuntoff, a co-inventor herein, discloses a dental impression wafer having a sheet carrier of strong pliable material sandwiched between deformable impression material such as bite wax. The wafer permits a precise visual indication of premature engagement of the teeth and bite deflection. The wafer however does not permit measurement of monitoring of the bite force and force exerted on the wafer by the patient during occlusal analysis, which analysis may suggest left/right muscular disbalance due possibly to premature contact or deflected contact between teeth of the maxilla and mandible. The force exerted during an occlusal analysis can now be monitored, and permanent records of the force exerted on either side of the mouth are readily obtainable. These records may be used to later compare the patient's muscle activity before and after correction and adaptation.

Briefly, the invention comprises a thin metallized film of polymer material having piezoelectric properties, the film being coated on all surfaces and edges with a conventional dental impression material, typically bite wax. The polymer film is preferably KYNAR ® piezofilm, a polyvinylidene fluoride product of Pennwalt Corporation, Philadelphia, Pa., assignee of the present invention, although copolymers of vinylidene fluoride have been found to work satisfactorily.

The wax retains visible impressions of the relative positions and shapes of the tooth crowns, as well as bite deflection and premature teeth engagement indicia. The wax should deform plastically without affecting the spatial relationship of the teeth, and normally such condition obtains if the carrier sheet thickness is maintained below about 0.025 mm, although the abovementioned patent suggests a value no greater than about 0.020 mm. The piezoelectric film material, on the other hand, permits force measurements to be precisely continuously monitored, which measurements may be permanently recorded by conventional means. If the carrier film (piezoelectric film) thickness is greater than about 0.025 mm, an artificial prematurity may result.

DETAILED DESCRIPTION OF THE INVENTION

Figure 1:
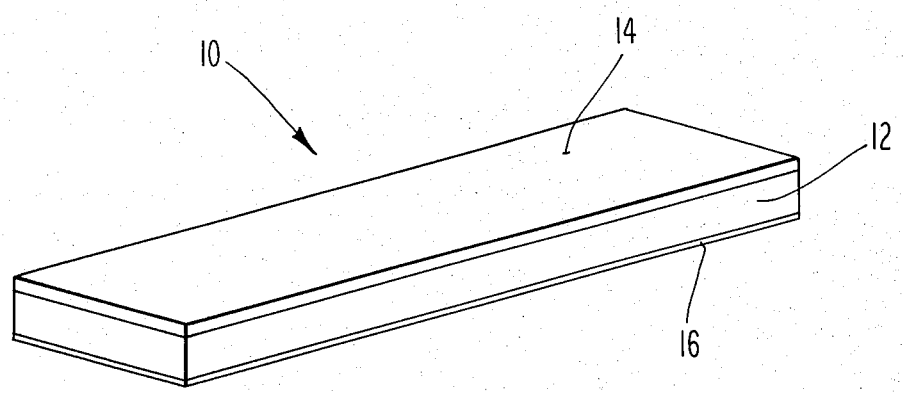
FIG. 1 is a perspective view of a strip of metal coated polymer film having piezoelectric properties.

In FIG. 1, piezofilm assembly 10 comprises uniaxially or biaxially oriented polymer film 12, preferably KYNAR ® piezofilm, having conventionally applied suitable metallized coatings 14 and 16, typically aluminum, secured to respective faces thereof. Coating 14 is preferably about 1000 Å thick, or about $0.1\mu$, to thereby provide about 0.60 ohms per square or sufficient electromagnetic interference shielding to the piezofilm 12. Coating 16 may be thinner, or only about 300 Å, or about $0.03\mu$, to provide about 10 ohms per square. Piezofilm assembly 10 is preferably no greater than about 0.025 mm in thickness to avoid any interference with normal interengagement of the teeth, although thicknesses considerably greater may be used at the expense of accuracy and preciseness. We have found that piezofilm assembly 10 thicknesses ranging between about 0.016 to 0.020 mm work satisfactorily.

Figure 2:
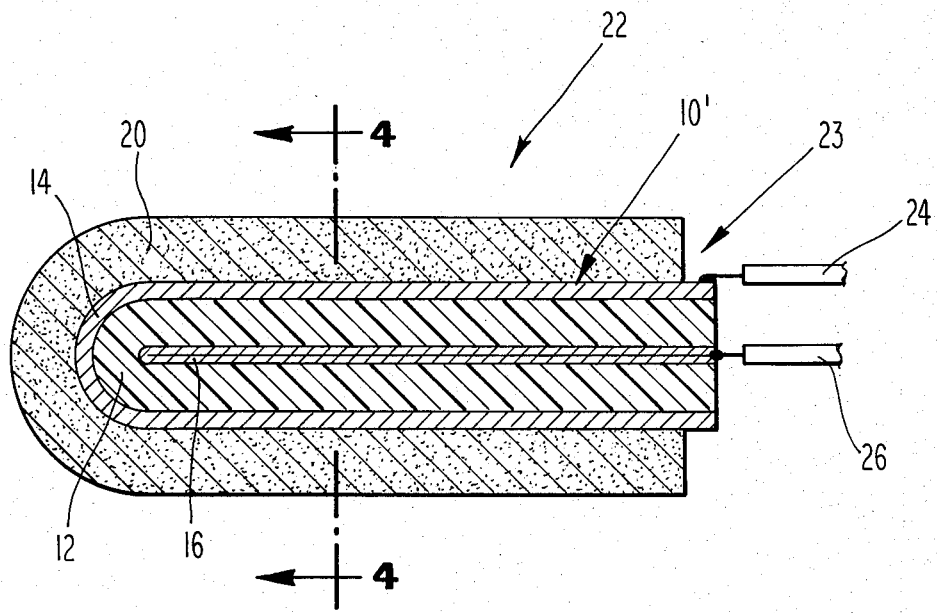
FIG. 2 is a sectional view of the strip of FIG. 1 folded to form the transducing element, the folded strip being substantially coated with dental impression material.

Thus, when coated piezofilm assembly 10 is folded, as shown exaggeratedly in FIG. 2, and piezofilm 12 measures $9.0\mu$ thick, while coatings 14 and 16 are $0.1\mu$ and $0.03\mu$ thick respectively, the folded piezofilm assembly 10' will have a total thickness of $18.26\mu$.

The folded piezofilm assembly 10' is provided with a layer of dental bite wax 20. The wax should be less than 0.5 mm thick, and preferably 0.35 mm. Wax 20 overlaps the folded piezofilm assembly 10' on each edge (except at front portion 23) by about ⅛" (FIG. 2) to form a dental strip or dental impression strip occlusal force indicator 22.

Figure 5:
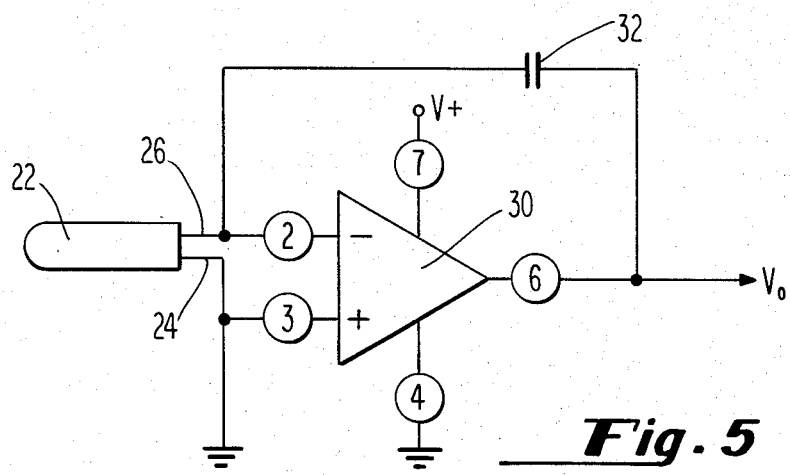
FIG. 5 is a schematic diagram of electronic means for converting voltages generated by the folded high impedance piezofilm strip to low impedance voltage outputs.

Wire leads from shielded coaxial cables 24 and 26 make contact to the metallized coatings 14 and 16 respectively; the high side 26, which may be + or −, is connected to the negative terminal of an IC operational amplifier 30 while the low side 24 is grounded with the positive terminal of op-amp 30 (FIG. 5).

Figure 3:
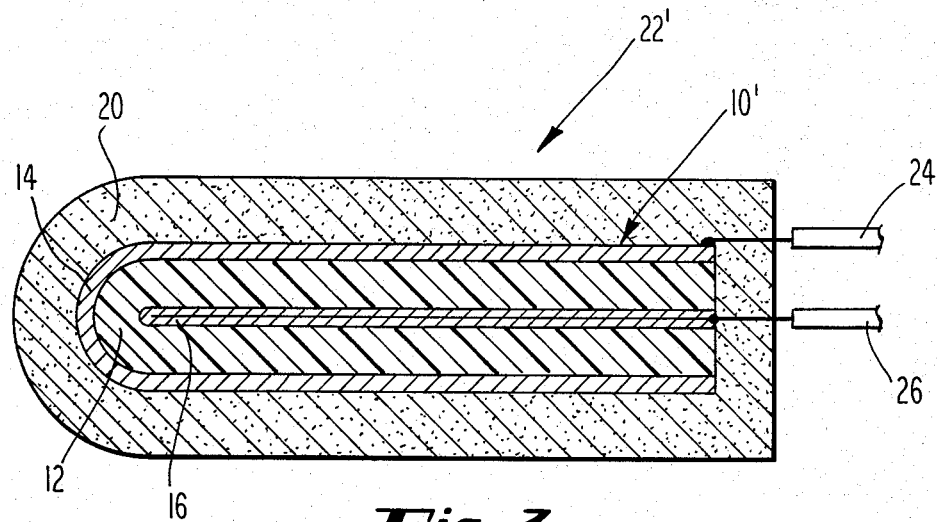
FIG. 3 is a sectional view of a modification of the folded strip of FIG. 2, the folded strip being completely coated with dental impression material.
Figure 4:
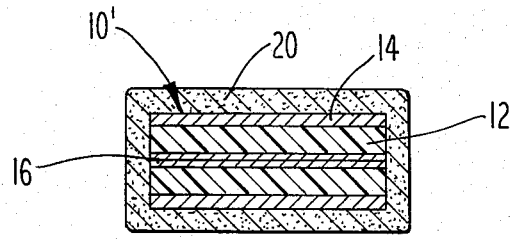
FIG. 4 is a sectional view of FIG. 2 taken along line 4—4 thereof.

In FIG. 3, folded piezofilm assembly 10' is provided with a layer of wax 20 completely therearound to form a dental impression strip occlusal force indicator 22'.

Op-amp 30 converts the high impedance output from the folded piezofilm assembly 10' to a low impedance voltage output which can be transmitted to a suitable display device (not shown) with no pickup of unwanted signals. The charge generated by folded piezofilm assembly 10' is collected by a feedback capacitor 32 whose voltage is measured as the output voltage of op-amp 30:

$$V_o(\tau) = (1/C)Q(\tau)$$

where
$V_o$ = voltage output of op-amp 30
$\tau$ = time
C = capacitance of capacitor 32
Q = closed circuit charge output of folded piezofilm assembly 10'

The numerals 2, 3, 4, 6 and 7 leading from op-amp 30 merely designate conventional pin connections.

Voltage output, $V_o$, is proportional to the time integral of the current output of folded piezofilm assembly 10' and increases as the force of the bite increases.

Voltage output, $V_o$, may be connected for display on a storage oscilloscope, or to a strip chart recorder if a permanent record of the bite force is desired, and to speaker means where amplitude or pitch may indicate the instantaneous value of the bite force.

Optionally, alternative electronic means for monitoring output voltages from the piezofilm assemblies may be utilized.

Separate strip occlusal force indicators 22 or 22' may be inserted in both sides of the mouth simultaneously to obtain data or information on first contact, high spots, disbalance, and the like. Also, one non-electrically active dental impression strip described in the aforementioned Shpuntoff patent may be used simultaneously with the occlusal force indicator of the present invention on opposite sides of the mouth in order to provide non-prejudiced bite monitoring.

The present occlusal force indicator may be used advantageously to monitor the occlusion of teeth other than natural.

For purposes of demonstration, the folded piezofilm assembly 10' may be coated with polytetrafluoroethylene, polyethylene, and the like, which is non-permanently deformable and reusable, and will not provide bite impressions, but will indicate to the dentist and patient that continuous monitoring and recording of forces exerted during occlusal analysis may readily be effected. The non-permanently deformable and reusable material may be up to several millimeters in thickness and may be coated over the piezofilm assembly 10' as is wax 20 (FIGS. 2 and 3) or in any other suitable manner.

We claim:

1. Occlusal force indicating device comprising polymer film means having a metallized coating on each face thereof to form a piezoelectric film assembly,
   a plastically deformable material coating in substantial contact with outer faces and edges of said piezofilm assembly, said piezofilm assembly comprising a single film folded upon itself to form a folded piezofilm assembly, and
   electrical means connected to said piezofilm assembly for conducting electrical output generated thereby to form said occlusal force indicating device, said electrical means comprising a shielded cable with a center lead connected to central metallized coatings and shielding connected to outermost layers of said metallized coatings, said output being generated when occlusal force is applied to said plastically deformable material.

2. Device of claim 1 wherein said plastically deformable material coating is in substantially complete contact with each face and edge of said folded piezofilm assembly.

3. Device of claim 2 wherein said polymer film comprises polarized polyvinylidene fluoride.

4. Device of claim 3 wherein said folded piezofilm assembly is less than about 0.025 mm thick.

5. Device of claim 4 wherein said folded piezofilm assembly is preferably between about 0.016 mm and 0.020 mm thick.

6. Device of claim 4 wherein said plastically deformable material coating is less than about 0.5 mm thick, and preferably about 0.35 mm thick.

7. Device of claim 6 wherein said plastically deformable material coating overlaps edges of said folded piezofilm assembly by about ⅛".

8. Device of claim 2 wherein said polymer film is a polarized copolymer of vinylidene fluoride.

9. Device of claim 2 wherein said shielded cable is connected to means for providing low impedance voltage outputs proportional to occlusal force exerted on said plastically deformable material coating, said low impedance voltage outputs connected to means for continuous monitoring thereof.

10. Device of claim 9 wherein said low impedance voltage outputs are operably connected to strip chart recorder means.

11. Device of claim 9 wherein said low impedance voltage outputs are operably connected to sound emitting means.

12. Device of claim 9 wherein said low impedance voltage outputs are operably connected to a storage oscilloscope.

13. Device of claim 1 wherein said plastically deformable material coating is in complete contact with each face and edge of said folded piezofilm assembly.

* * * * *

UNITED STATES PATENT AND TRADEMARK OFFICE
CERTIFICATE OF CORRECTION

PATENT NO. : 4,488,873
DATED : December 18, 1984
INVENTOR(S) : Philip E. Bloomfield et al It is certified that error appears in the above-identified patent and that said Letters Patent are hereby corrected as shown below:

IN THE ASSIGNEE'S SECTION OF THE FRONT PAGE OF THE PATENT:

Change "Pennwalt Corporation, Philadelphia, Pa" to --Harry Shpuntoff, Jackson Heights, N.Y.--.

IN THE SPECIFICATION

Column 1, lines 40-41, delete "assignee of the present invention,".

Signed and Sealed this

First Day of October 1985

[SEAL]

Attest:

DONALD J. QUIGG

Attesting Officer

Commissioner of Patents and Trademarks—Designate